United States Patent [19]

Fujimoto

[11] 4,009,022
[45] Feb. 22, 1977

[54] SELECTIVE ANTAGONISTS FOR TRIAZINE HERBICIDES

[75] Inventor: Ted Tsutomu Fujimoto, Warminster, Pa.

[73] Assignee: Rohm and Haas Company, Philadelphia, Pa.

[22] Filed: Oct. 30, 1975

[21] Appl. No.: 627,482

[52] U.S. Cl. .............................. 71/93; 260/566 B
[51] Int. Cl.² ........................................ A01N 9/22
[58] Field of Search ........................................ 71/93

[56] References Cited

UNITED STATES PATENTS

| | | | |
|---|---|---|---|
| 3,923,494 | 12/1975 | Teach | 71/93 X |
| 3,930,836 | 1/1976 | Arneklev | 71/93 |
| 3,930,839 | 1/1976 | Arneklev | 71/93 X |

*Primary Examiner*—Joseph Paul Brust
*Attorney, Agent, or Firm*—William E. Lambert, III

[57] ABSTRACT

Compounds of the formula

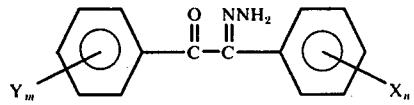

wherein X and Y are halogen, alkyl, alkoxy, trifluoromethyl, or nitro, and $n$ and $m$ are 0 to 3 are useful in reducing the phytotoxicity of triazine herbicides towards agronomic crops, particularly in reducing the phytotoxicity of residual triazine herbicide in rotated crops.

15 Claims, No Drawings

SELECTIVE ANTAGONISTS FOR TRIAZINE HERBICIDES

THE DISCLOSURE

This invention relates to benzil monohydrazone and certain of its derivatives and to the use of these compounds as safening agents for selectively reducing the phytotoxicity of triazine herbicides.

Among the selective herbicides currently of commercial significance, the triazines are economically the most important class. However, while triazine herbicides are useful in controlling a broad spectrum of weeds, their application has been somewhat limited by their phytotoxicity to many crops. For example, atrazine, which can control most of the weed problems in soybean crops, cannot be employed because of its phytotoxicity to soybeans. Futhermore, triazines often possess undesirable residual activity that can prevent their use where crop rotation or multiple crop plantings are necessary or desirable. Consequently, atrazine is widely used as a selective herbicide in corn crops but usually is not employed where soybeans are to follow the corn. Thus, compounds which selectively inhibit the phytotoxicity of triazine herbicides would be extremely valuable as a means to extend the area of utility of these herbicides.

It has now been found that benzil monohydrazones reduce the phytotoxicity of triazine herbicides without significantly adversely affecting the general herbicidal activity of the triazines, thus safening the triazine herbicides for use in otherwise sensitive crops. The benzil monohydrazones of the invention have the formula

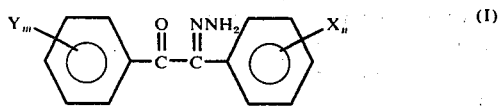

wherein
X and Y are individually halogen, preferably chlorine, ($C_1$–$C_4$)alkyl, preferably methyl, ($C_1$–$C_4$)alkoxy, preferably methoxy, trifluoromethyl, or nitro, and
$n$ and $m$ are 0, 1, 2, or 3.

In a preferred embodiment of the invention, X and Y are chlorine, and $n$ and $m$ are 0 or 1.

Typical compounds embraced by Formula I include:

benzil hydrazone,
4-chlorobenzil hydrazone,
3-chlorobenzil hydrazone,
2,4-dichlorobenzil hydrazone,
2'-chlorobenzil hydrazone,
4'-chlorobenzil hydrazone,
2',4',6'-trichlorobenzil hydrazone,
2'-bromobenzil hydrazone,
2'-fluoro-4'-chlorobenzil hydrazone,
3-methoxybenzil hydrazone,
3,3'-dimethoxybenzil hydrazone,
4'-n-propoxybenzil hydrazone,
4,4'-dimethylbenzil hydrazone,
3-nitrobenzil hydrazone,
4-trifluoromethylbenzil hydrazone,
3,3'-bis(trifluoromethyl)benzil hydrazone,
2,2'-diethoxybenzil hydrazone, and the like.

The hydrazones of the invention can be used to safen and reduce selectively the phytotoxicity of a wide variety of triazines, including atrazine, simazine, metribuzin [4-amine-6-(1,1-dimethylethyl)-3-methylthio-1,2,4-triazin-5-(4H)one], ametryn, prometryne, propazine, procyazine, terbutryn, and the like. In a preferred embodiment of the invention, the hydrazones are used as antagonists to atrazine.

The benzil hydrazones of the invention are particularly useful in crop rotation situations where atrazine has been used as a herbicide in the first crop. For example, when a triazine such as atrazine has been used as the herbicide for a corn crop, the same field can be used for soybeans as a following or next season crop by applying to the field prior to or at the same time of planting the next crop a hydrazone of the invention, thereby reducing the phytotoxicity of residual triazine to the following crop. Other suitable crops which can be rotated with a crop in which a triazine has been used as a herbicide and protected against phytotoxicity from the residual triazine by the hydrazones of the invention include wheat, barley, oats, cotton, vegetable crops, and the like. When used as a protectant in a rotated crop, the hydrazone will generally be applied at a rate of about 1 about 30, preferably about 5 to about 20 pounds per acre. When used as a crop rotation protectant, the hydrazone can be applied at any time prior to the emergence of the following crop, but will usually be applied after harvesting the first crop and prior to or simultaneously with the planting of the following crop.

The hydrazones of the invention can also be applied as a seed treatment. Generally, the hydrazone will be applied to the seed of the crop to be protected at a rate of about 1 to about 32 ounces, preferably about 4 to about 16 ounces, of hydrazone per 100 pounds of seed. Another useful method of applying the compounds of the invention is by an in-furrow treatment. In this type of treatment, the hydrazone is applied in a narrow band directly onto the seed after the planter has dropped the seed into the furrow, but before the seed is covered with soil. When an in-furrow treatment is employed, the hydrazone is usually applied at a nominal rate of about 5 to about 20 pounds per acre, which is equivalent to a much lower overall rate, thus significantly reducing the actual quantity of the hydrazone necessary to accomplish the desired safening.

The benzil hydrazones of the invention can also be used to reduce the phytotoxicity of triazine herbicides to various crops. For example, by using a benzil hydrazone in a combination treatment with a triazine such as atrazine, simazine, or metribuzin in preemergence applications, weed control and improved crop tolerance can be obtained in crops such as soybeans which are sensitive to the triazines. Other crops in which this combination treatment can be advantageously employed include sorghum, cotton, wheat, and the like. When used in a combination treatment, the benzil hydrazone and the triazine can be applied either simultaneously or sequentially generally in a weight ratio of hydrazone to triazine of about 30:1 to 1:1, preferably about 20:1 to 5:1, and at an application rate in the range of about 1 to about 40, preferably about 5 to about 20, pounds per acre of the hydrazone and about ⅛ to about 10, preferably about ¼ to about 4, pounds per acre of the triazine. Multiple applications of the hydrazone can also be used to lengthen the period of phytotoxicity reduction in the crop.

The compounds of the invention can be applied to the growth medium or to plants to be treated either by itself or, as is generally done, as a component in a agricultural composition or formulation which also comprises an agronomically acceptable carrier. By agronomically acceptable carrier is meant any substance which can be used to dissolve, disperse, or diffuse a compound in the composition without impairing the effectiveness of the compound and which by itself has not detrimental effect on the soil, equipment, crops, or agronomic environment. Mixtures of the compounds of the invention may also be used in any of these formulations. The compositions of the invention can be either solid or liquid formulations or solutions. For example, the compounds can be formulated as wettable powders, dusts, granular formulations, aerosols, or flowable emulsion concentrates. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

The compounds of this invention can be dissolved in any appropriate solvent. Examples of solvents which are useful in the practice of this invention include alcohols, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% by weight with a preferred range being about 25% to about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98% by weight, preferably about 40% to 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% by weight of the active ingredient are commonly made and are subsequently diluted to about 1% to 10% use concentration.

Granular formulations can be prepared by impregnating a solid such as granular fuller's earth, vermiculite, ground corn cobs, seed hulls, including bran or other grain-hulls, or similar material. A solution of one or more of the compounds in a volatile organic solvent can be sprayed or mixed with the granular solid and the solvent then removed by evaporation. The granular material can have any suitable size, with a preferable size range of 16 to 60 mesh. The active ingredient will usually comprise about 2 to 15% by weight of the granular formulation.

The compounds of the invention can also be mixed with fertilizers or fertilizing materials before their application. In one type of solid fertilizing composition in which the compounds can be used, particles of a fertilizer or fertilizing ingredients, such as ammonium sulfate, ammonium nitrate, or ammonium phosphate, can be coated with one or more of the ethers. The solid compounds and solid fertilizing material can also be admixed in mixing or blending equipment, or they can be incorporated with fertilizers in granular formulations. Any relative proportion of compound and fertilizer can be used which is suitable for the crops and weeds to be treated. The active ingredient will commonly be from about 5% to about 25% by weight of the fertilizing composition. These compositions provide fertilizing materials which promote the rapid growth of desired plants, and at the same time control the growth of undesired plants.

The compounds of the invention can be applied as sprays by methods commonly employed, such as conventional high-gallonage hydraulic sprays, low gallonage sprays, air-blast spray, aerial sprays and dusts. For low volume applications a solution of the compound is usually used. The dilution and rate of application will usually depend upon such factors as the type of equipment employed, the method of application, and the area to be treated.

The hydrazones of the invention can be prepared by any suitable preparative technique. In one useful method, they are prepared by reacting a suitably-substituted benzil with hydrazine. This reaction is generally carried out at a temperature of about 20° to about 150° C, in an inert, preferably polar, solvent such as methanol, ethanol, propanol, or aqueous ethanol, glyme, dioxane, or acetonitrile. Generally, the reagents are used in an equimolar amount, although an excess of hydrazine can be used. An acid catalyst, such as acetic acid or sulfuric acid, can also be employed.

The benzils which are used as starting materials in this reaction are prepared by several conventional synthetic routes, including oxidation of benzoins synthesized by a mixed benzoin condensation, oxidation of diaryl acetylenes, $\alpha$-oxidation of deoxybenzoins, and the like. The benzoins can be oxidized using an oxidizing agent such as air or oxygen, nitric acid, cupric sulfate, selenium dioxide, potassium permanganate, sodium or potassium dichromate, ceric salts, manganese dioxide, or the like. The oxidations are generally carried out at a temperature of about −10° to about 150° C in a suitable inert oxidativelystable solvent, appropriate to the particular oxidizing agent, using an excess of the oxidizing agent. Suitable solvents include hydrocarbons, chlorinated hydrocarbons, pyridine, dioxane, tetrahydrofuran, acetone, dimethyl formamide, aqueous sulfuric acid, water, acetic acid, acetic anhydride, and the like. The diaryl acetylenes can be oxidized using selenium dioxide in water, acetic aicd, t-butanol, dioxane, or the like or using potassium permanganate in water, benzene or other hydrocarbon or the like, using a crown ether catalyst. The reaction is generally run at a temperature of about 20° to about 150° C, using an excess of the oxidizing agent. Oxidations of the deoxybenzoins can be effected using selenium dioxide, potassium permanganate, chromic anhydride, oxygen, or the like using a metallic catalyst. The oxidation is generally run at a temperature of about 20° to about 200° C, using an excess of the oxidizing agent, in an inert oxidatively-stable solvent such as acetic anhydride, acetic acid, pyridine, water, dioxane, or the like.

In another useful method, α-bromodeoxybenzoins, which are prepared by bromination of deoxybenzoins, are reacted with excess hydrazine. The bromination reaction usually employs a brominating agent such as potassium bromide, cupric bromide, phenyltrimethylammonium perbromide, pyridinium hydrobromide perbromide, N,N-diethyl-2-cyano-2-bromoacetamide, or the like, in an equimolar amount with the deoxybenzoin. This reaction can be carried out conveniently at a temperature of about 0° to about 150° C in a hydrocarbon, a chlorinated hydrocarbon, ethyl acetate, acetic acid, acetic anhydride, dimethylformamide, an ether, or the like, as a solvent. The α-bromodeoxybenzoin is then treated with an excess of hydrazine in a polar organic solvent, such as ethanol or aqueous ethanol, acetonitrile, dioxane, glyme, or dimethylformamide, under buffered conditions at a temperature of about 20° to about 150° C. The deoxybenzoins are usually obtained either by the Grignard coupling of a substituted benzonitrile with a substituted benzylmagnesium halide, or the corresponding substituted benzyl lithium or by the Friedel-Crafts acylation of a substituted benzene with a substituted phenylacetyl chloride. The Grignard reaction is carried out in a solvent such as tetrahydrofuran or ether at a temperature of about 0° to about 150° C, and an equimolar amount of the benzylmagnesium halide or benzyl lithium and benzonitrile are used. The Friedel-Crafts acylation is generally run at a temperature of about 0° to about 200° C, using the substituted benzene as the solvent, or using carbon disulfide or a chlorinated hydrocarbon as a diluent. A Lewis acid, such as ferric chloride, stannic chloride, titanium tetrachloride, aluminum trichloride, boron trifluoride, zinc chloride, hydrogen fluoride, concentrated sulfuric acid, phosphorus pentoxide, or the like, is also used in catalytic or stoichiometric amounts.

The following examples will further illustrate this invention, but are not intended to limit it in any way. In Table I, typical hydrazones of the invention are listed, along with their melting points and elemental analyses. Specific, illustrative preparations of the compounds of Examples 1, 2, 6, 8, and 12 are set forth after Table I.

TABLE I

Benzil Hydrazones - Physical Data

Structure: Y-C$_6$H$_4$-C(=O)-C(=N-NH$_2$)-C$_6$H$_4$-X

| Example No. | X | Y | M.P. | Empirical Formula | Elt. | Calc. | Found |
|---|---|---|---|---|---|---|---|
| 1 | 4-CH$_3$ | 4-CH$_3$ | 137–140° | C$_{16}$H$_{16}$N$_2$O | C | 76.16 | 75.82 |
|   |   |   |   |   | H | 6.39 | 6.34 |
|   |   |   |   |   | N | 11.11 | 10.92 |
| 2 | 4-NO$_2$ | H | 105–107° | C$_{14}$H$_{11}$N$_3$O$_3$ | C | 62.45 | 62.69 |
|   |   |   |   |   | H | 4.12 | 4.21 |
|   |   |   |   |   | N | 15.61 | 15.57 |
| 3 | H | 4-CH$_3$ | 106–115° | C$_{15}$H$_{14}$N$_2$O | C | 75.60 | 75.88 |
|   |   |   |   |   | H | 5.92 | 6.02 |
|   |   |   |   |   | N | 11.76 | 11.31 |
| 4 | 4-CH$_3$ | H | 149–151° | C$_{15}$H$_{14}$N$_2$O | C | 75.60 | 75.32 |
|   |   |   |   |   | H | 5.92 | 5.90 |
|   |   |   |   |   | N | 11.76 | 11.48 |
| 5 | 3-CH$_3$ | H | 105–107° | C$_{15}$H$_{14}$N$_2$O | C | 75.60 | 74.74 |
|   |   |   |   |   | H | 5.92 | 5.89 |
|   |   |   |   |   | N | 11.76 | 11.60 |
| 6 | H | 3-Cl | 116–118° | C$_{14}$H$_{11}$ClN$_2$O | C | 64.99 | 64.59 |
|   |   |   |   |   | H | 4.29 | 4.61 |
|   |   |   |   |   | N | 10.83 | 10.27 |
|   |   |   |   |   | Cl | 13.70 | 13.67 |
| 7 | H | 3-CH$_3$ | 118–124° | C$_{15}$H$_{14}$N$_2$O | C | 75.60 | 75.72 |
|   |   |   |   |   | H | 5.92 | 6.00 |
|   |   |   |   |   | N | 11.76 | 11.92 |
| 8 | 4-Cl | H | 135–137° | C$_{14}$H$_{11}$ClN$_2$O | C | 64.99 | 65.08 |
|   |   |   |   |   | H | 4.29 | 4.36 |
|   |   |   |   |   | N | 10.83 | 10.95 |
|   |   |   |   |   | Cl | 13.70 | 13.58 |
| 9 | H | 4-Cl | 135–137° | C$_{14}$H$_{11}$ClN$_2$O | C | 64.99 | 64.44 |
|   |   |   |   |   | H | 4.29 | 4.21 |
|   |   |   |   |   | N | 10.83 | 10.49 |
|   |   |   |   |   | Cl | 13.70 | 14.13 |
| 10 | 2-Cl | H | 131–133° | C$_{14}$H$_{11}$ClN$_2$O | C | 64.99 | 64.94 |
|   |   |   |   |   | H | 4.29 | 4.28 |
|   |   |   |   |   | N | 10.83 | 10.66 |
|   |   |   |   |   | Cl | 13.70 | 13.83 |
| 11 | 3-Cl | H | 110–112° | C$_{14}$H$_{11}$ClN$_2$O | C | 64.99 | 65.05 |
|   |   |   |   |   | H | 4.29 | 4.23 |
|   |   |   |   |   | N | 10.83 | 10.90 |
|   |   |   |   |   | Cl | 13.70 | 14.02 |
| 12 | 3-OCH$_3$ | 3-OCH$_3$ | 109–111° | C$_{16}$H$_{16}$N$_2$O$_3$ | C | 67.59 | 67.32 |
|   |   |   |   |   | H | 5.67 | 5.68 |
|   |   |   |   |   | N | 9.88 | 9.63 |
| 13 | 4-OCH$_3$ | H | 135–138° | C$_{15}$H$_{14}$N$_2$O$_2$ | C | 70.84 | 67.59 |
|   |   |   |   |   | H | 5.55 | 5.37 |
|   |   |   |   |   | N | 11.02 | 10.10 |
| 14 | H | 2-Cl | 155–158° | C$_{14}$H$_{11}$ClN$_2$O | C | 64.99 | 64.68 |
|   |   |   |   |   | H | 4.29 | 4.22 |
|   |   |   |   |   | N | 10.83 | 10.68 |
|   |   |   |   |   | Cl | 13.70 | 13.82 |

EXAMPLE 1

Preparation of 4,4'-dimethylbenzil hydrazone

To a hot solution of 10 g 4,4'-dimethylbenzil in 20 ml of ethanol is added 2.1 g of hydrazine hydrate. After a few minutes at reflux, a solid begins to crystallize. Heating is continued for 10 min. and the solution cooled slowly to 0° C. The solid is filtered off and washed with cold ethanol. The product is recrystallized from ethanol. Yield 7.1 g. M.P. 137°–140°.

EXAMPLE 2

Preparation of 4-nitrobenzil hydrazone

Benzoin, 60 g, is suspended in 600 ml acetic anhydride and 60 ml concentrated sulfuric acid is added under ice cooling. Under continued ice cooling, 33 g potassium nitrate is added in small portions. The reaction is stirred at room temperature for two days and poured over ice. The aqeuous portion is decanted off and the remaining oil is taken up in ether, washed with water, sodium bicarbonate solution, dried over potassium carbonate and stripped. The oil residue is added dropwise to concentrated nitric acid at 0°, followed by heating gently on a steam bath for 2 hours. After cooling, the solution is poured over ice. The solid which forms is removed by filtration (~40 g) and recrystallized three times from glacial acetic acid, to yield 5.5 g of a yellow solid, 4-nitrobenzil. To a solution of 0.7 g hydrazine hydrate in 50 ml ethanol is added a suspension of 4-nitrobenzil, 5.1 g, in 150 ml of ethanol. The reaction is heated on a steam bath for 1 hour and cooled. Plate-like crystals separate out and are removed by filtration. Yield 3.5 g. The product is recrystallized from 200 ml ethanol. M.P. 166°–173°.

EXAMPLE 6

Preparation of 3'-chlorobenzil hydrazone

Bromine, 6.48 g, in 20 ml of chloroform is added drop-wise to 10 g of 3-chlorodeoxybenzoin, prepared as in Example 15, in 30 ml of refluxing chloroform. After addition is complete, the solution is refluxed 1 hour, cooled and the solvent removed. The residue is dissolved in 40 ml ethanol and 120 ml of a 50% aqueous ethanolic solution containing 13.12 g sodium acetate and 5.12 g hydrazine hydrate is added. After the initial exotherm, the reaction is refluxed for 10 minutes and cooled to crystallize product. Yield 3.4 g. Material is recrystallized from aqueousthanol. M.P. 116°–188° C. Similarly prepared are 4'-methylbenzil hydrazone, 3'-methylbenzil hydrazone, 3-chlorobenzil hydrazone, 3-methylbenzil hydrazone, 4-chlorobenzil hydrazone, 3'-chlorobenzil hydrazone, 3'-chlorobenzil hydrazone, 4'-methoxybenzil hydrazone, 2-chlorobenzil hydrazone.

EXAMPLE 8

Preparation of 4-chlorobenzil hydrazone

A benzene solution containing 51.2 g 4-chlorophenylacetic acid and 39.3 g thionyl chloride is refluxed for 6 hours and the solvent removed. The crude reaction product is added dropwise to a slurry of 40 g aluminum chloride in 200 ml benzene maintaining the temperature below 50° C. After addition the reaction is refluxed for 1.5 hours. After cooling, the mixture is poured into ice and the resulting white solid is separated yielding 61.3 g of crude product. The product is taken up in methylene chloride and washed with 5% sodium hydroxide solution followed by water, dried over sodium sulfate and stripped yielding 49.3 g (71%) of >95% pure 4'-chlorodeoxybenzoin. 15 g of 4-chlorodeoxybenzoin is dissolved in 105 ml pyridine. An aqueous solution containing 15 g potassium permanganate is added and the reaction stirred for 6 hours at room temperature using dry ice to buffer the pH near 7. The mixture is extracted with methylene chloride, the extract washed with water, dried over Na$_2$SO$_4$ and stripped. The residue is recrystallized from ethanol yielding 6.1 g of white plate-like crystals which is identified as starting material. Concentration of the mother liquor yields 4 g of 4-chlorobenzil.

To a solution of 3.5 g 4-chlorobenzil in 15 ml ethanol is added 0.45 g anhydrous hydrazine. The solution is refluxed for 1 hour, filtered and water added to the cloud point, and allowed to crystallize yielding 2.3 g of 4-chlorobenzoin hydrazone.

EXAMPLE 12

Preparation of 3,3''-dimethoxybenzil hydrazone

To a solution of 1.0 g hydrazine hydrate in 25 ml ethanol is added a warm solution of 3,3'-dimethoxybenzil, 7.0 g in 125 ml ethanol. The solution is heated to 65° C for 48 hours. Three drops of acetic acid are added and heating is continued for 48 hours. The solution is concentrated, diluted with 100 ml water and extracted with methylene chloride. The organic layer is removed, dried over magnesium sulfate and the solvent removed. The oily residue is chromatographed on 200 g of BioSil-A using chloroform-benzene mixtures. Elution of product is completed with methylene chloride. The product from chromatography is recrystallized from chloroform-hexane yielding 2.8 g of pale yellow needles. M.P. 109°–110.5°.

EXAMPLE 15

Preparation of 4-chloro deoxybenzoin

To a 1-liter, three-neck flask is added 9.72 g of magnesium and 200 ml ether. A solution of 38 g benzyl chloride in ether is added at such a rate that gentle reflux is maintained. After reflux subsides, 33 g of 4-chlorobenzonitrile is added dropwise. The mixture is refluxed overnight. After cooling, the reaction is treated with concentrated HCl and stirred for 2 hours. The ether phase is separated, dried over Na$_2$SO$_4$, and the solvent removed yielding 53.4 g of solid. Recrystallization from carbon tetrachloride-hexane yields 40 g of 4-chlorodeoxybenzoin, M.P. 104.5°–106° C. Similarly prepared are 3-chloro deoxybenzoin, 3-methyl deoxybenzoin, 4-methyl deoxybenzoin, 3'-methyl deoxybenzoin, 4'-methyl deoxybenzoin, 3'-chloro deoxybenzoin, 2'-chloro deoxybenzoin, 2-chloro deoxybenzoin.

The following examples show the use of the monohydrazones of the invention in reducing the phytotoxicity of triazine herbicides.

EXAMPLE 16

Three tests are used to evaluate the activity of the hydrazones of the invention in reducing the phytotoxicity of triazine herbicides when applied to the soil.

Test 1

In this test the antidotes and atrazine are sprayed on the soil surface and then incorporated into the top ½ inch.

Test 2

The antidotes and atrazine are sprayed and soil incorporated as in Test 1; however, the treated soil is aged for 4 weeks prior to planting.

Test 3

In this test, unsubstituted benzil hydrazone is sprayed onto the flats at the seed level, the cover soil is then placed over the seed, and either atrazine or metribuzin sprayed onto the soil surface. Four replicates are employed.

Table II summarizes results obtained using various benzil hydrazones in Tests 1 and 2. Table III summarizes results obtained using unsubstituted benzil hydrazone in Test 3.

TABLE II

Benzil Hydrazones as Atrazine Antidotes

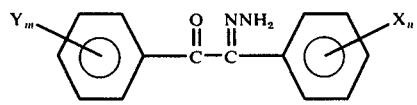

| X | Y | Rate of Hydrazone (lb/A) | Rate of Atrazine (lb/A) | Aged Soil | Soybean Injury (% Kill) |
|---|---|---|---|---|---|
| H | H | 10 | 1.5 | No | 20 |
| H | H | 10 | 1.5 | 4 wks. | 20 |
| 4-CH₃ | 4-CH₃ | 10 | 1.5 | 4 wks. | 30 |
| 4-NO₂ | H | 10 | 1.5 | No | 70 |
| 4-NO₂ | H | 10 | 1.5 | 4 wks. | 27 |
| H | 4-CH₃ | 10 | 1.5 | No | 50 |
| H | 4-CH₃ | 10 | 1.5 | 4 wks. | 10 |
| 4-CH₃ | H | 10 | 1.5 | No | 60 |
| 4-CH₃ | H | 10 | 1.5 | 4 wks. | 40 |
| H | 3-Cl | 10 | 1.5 | No | 60 |
| H | 3-Cl | 10 | 1.5 | 4 wks. | 33 |
| H | 3-CH₃ | 10 | 1.5 | No | 50 |
| 4-Cl | H | 10 | 1.5 | 4 wks. | 20 |
| H | 4-Cl | 10 | 1.5 | No | 20 |
| H | 4-Cl | 10 | 1.5 | 4 wks. | 27 |
| 2-Cl | H | 10 | 1.5 | 4 wks. | 30 |
| 3-Cl | H | 10 | 1.5 | No | 10 |
| 3-Cl | H | 10 | 1.5 | 4 wks. | 30 |
| 3-OCH₃ | H | 10 | 1.5 | No | 40 |
| 3-OCH₃ | H | 10 | 1.5 | 4 wks. | 30 |
| H | 2-Cl | 10 | 1.5 | No | 60 |
| H | 2-Cl | 10 | 1.5 | 4 wks. | 47 |
| Control | | 0 | 1.5 | No | 58 |
| Control | | 0 | 1.5 | 4 wks. | 60 |

TABLE III

| Herbicide | Rate of Herbicide (lb/A) | Rate of Hydrazone (lb/A) | Soybean Injury (% Kill) |
|---|---|---|---|
| metribuzin | 1 | 0 | 30 |
| metribuzin | 1.5 | 0 | 67 |
| metribuzin | 1 | 10 | 0 |
| metribuzin | 1.5 | 10 | 13 |
| atrazine | 2 | 0 | 77 |
| atrazine | 2 | 10 | 30 |
| none | 0 | 10 | 0 |

It is to be understood that changes and variations may be made without departing from the spirit and scope of the invention as defined by the appended claims.

I claim:

1. A method for reducing the phytotoxicity of a triazine herbicide selected from the group consisting of atrazine, simazine, metribuzin, ametryn, prometryne, propazine, procyazine, and terbutryn to an agronomic crop to which the triazine herbicide has been applied which comprises applying to the locus of the crop, prior to emergence of the crop, an effective amount of a compound of the formula

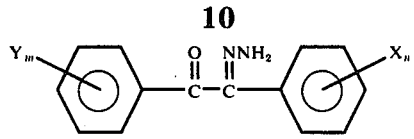

wherein
X and Y are individually halogen, $(C_1-C_4)$alkyl, $(C_1-C_4)$alkoxy, trifluoromethyl, or nitro, and
n and m are 0 to 3, at a rate of about 1 to about 30 pounds per acre.

2. The method of claim 1 wherein the triazine herbicide is atrazine or metribuzin.

3. The method of claim 2 wherein the weight ratio of compound to triazine herbicide of about 30:1 to 1.1 is employed.

4. The method of claim 3 wherein the triazine herbicide has been applied to the locus of the crop prior to the planting of the crop.

5. The method of claim 4 wherein the herbicide is atrazine.

6. The method of claim 5 wherein the crop is soybeans.

7. The method of claim 5 wherein n and m are 0.

8. The method of claim 5 wherein Y is chlorine, m is 1, and n is 0.

9. The method of claim 4 wherein the herbicide i metribuzin.

10. A method for selectively controlling weeds in an agronomic crop to which a triazine herbicide selected from the group consisting of atrazine, simazine, metribuzin, ametryn, prometryne, propazine, procyazine, and terbutryn is phytotoxic which comprises applying to the locus of the crop, prior to emergence of the crop, a herbicidally effective amount of the triazine herbicide and a compound of the formula

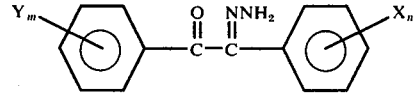

wherein
X and Y are individually halogen, $(C_1-C_4)$alkyl, $(C_1-C_4)$alkoxy, trifluoromethyl, or nitro, and
n and m are 0 to 3, in a weight ratio of compound to triazine herbicide of about 30:1 to 1:1.

11. The method of claim 10 wherein the compound is applied at a rate of about 1 to about 30 pounds per acre.

12. A safened herbicidal composition which comprises an effective amount of a triazine herbicide selected from the group consisting of atrazine, simazine, metribuzin, ametryn, prometryne, propazine, procyazine, and terbutryn and a safening amount of a compound of the formula wherein
X and Y are individually halogen, $(C_1-C_4)$alkyl, $(C_1-C_4)$alkoxy, trifluoromethyl, or nitro, and
n and m are 0 to 3, in a weight ratio of compound to triazine herbicide of about 30:1 to 1:1.

13. The composition of claim 12 wherein the herbicide is atrazine or metribuzin.

14. The composition of claim 13 wherein the n and m are 0.

15. The composition of claim 13 wherein Y is chlorine, m is 1, and n is 0.